United States Patent [19]

Mansat

[11] Patent Number: 5,074,880
[45] Date of Patent: Dec. 24, 1991

[54] ANCHORING DEVICE FOR KNEE PROSTHESIS

[75] Inventor: Christian Mansat, Balma, France
[73] Assignee: S.P.O.R.T., Custines, France
[21] Appl. No.: 452,752
[22] Filed: Dec. 19, 1989
[30] Foreign Application Priority Data Dec. 20, 1988 [FR] France .................. 88 17159

[51] Int. Cl.⁵ .................. A61F 2/38; A61F 2/30
[52] U.S. Cl. .................. 623/20; 623/16; 623/18
[58] Field of Search .................. 623/20, 18, 16

[56] References Cited

U.S. PATENT DOCUMENTS 4,743,261  5/1988  Epinette .................. 623/20
4,834,081  5/1989  Vanzile .................. 623/20

FOREIGN PATENT DOCUMENTS 3535112  4/1987  Fed. Rep. of Germany ........ 623/20
2585236  1/1987  France .................. 623/20

Primary Examiner—Ronald Frinks
Attorney, Agent, or Firm—Weiser & Stapler

[57] ABSTRACT

Anchoring device for a knee prosthesis of the unicompartmental or bicompartmental type, the said prosthesis comprising a tibial plateau provided on its tibial bearing face with anchoring grooves of dovetailed profile forming a grid pattern, characterized in that the anchoring is achieved by an anchoring crosspiece (7) inserted in the tibia and provided on its upper face with a stud (6) complementary to the groove forming a notch and engaging in the latter.

20 Claims, 1 Drawing Sheet

FIG. 1
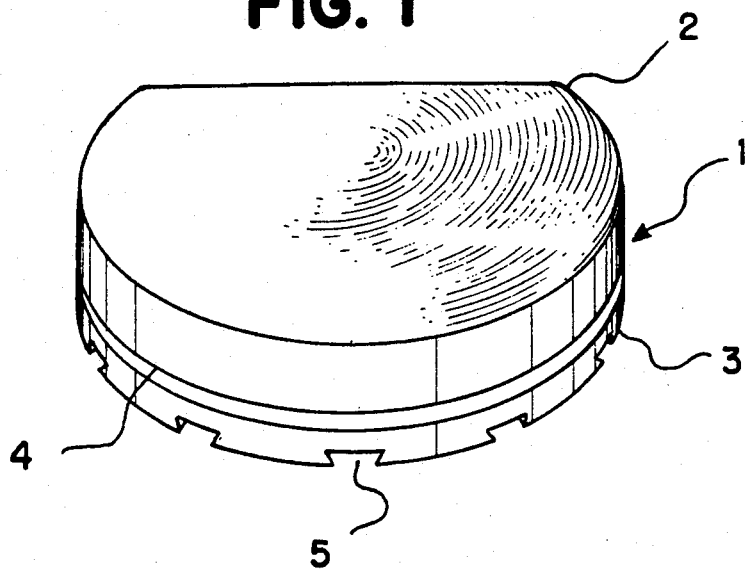
FIG. 2
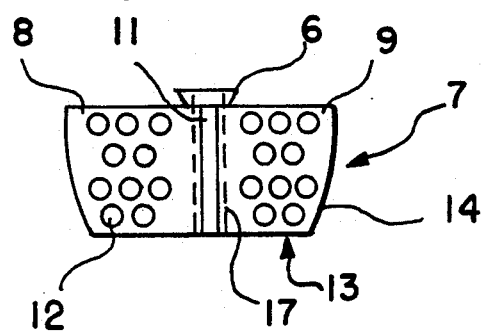
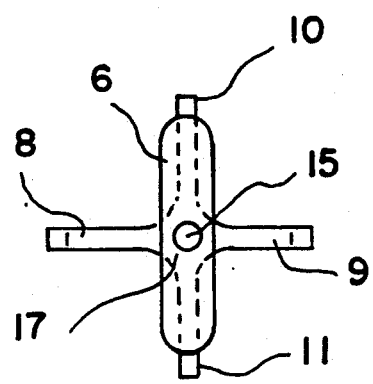
FIG. 3

ANCHORING DEVICE FOR KNEE PROSTHESIS

The present invention relates to an improvement made to anchoring devices for a knee prosthesis of the unicompartmental or bicompartmental type, the said prosthesis comprising a tibial plateau provided on its tibial bearing face with anchoring grooves of dovetailed profile forming a grid pattern.

Prostheses of this type are known per se.

They have been the subject of, for example, Patent FR 2,585,236, to which reference is expressly made here as the state of the art for existing anchoring systems.

The grooves of the tibial plateau are intended to strengthen the anchoring with the aid of a cement on the tibia, after formation of a plateau on the latter.

It is observed that the anchoring obtained is not always satisfactory.

According to the invention, this disadvantage is overcome by providing an improvement to the anchoring devices for a knee prosthesis of the unicompartmental or bicompartmental type, the said prosthesis comprising a tibial plateau provided on its tibial bearing face with anchoring grooves of dovetailed profile forming a grid pattern, characterized in that the anchoring is achieved by an anchoring crosspiece inserted in the tibia and provided on its upper face with a stud complementary to the groove forming a notch and engaging in the latter.

The wings of the crosspiece will preferably be provided with openings permitting osseous regeneration through the said crosspiece.

This structure simultaneously provides a seat for the tibial plateau and a locking of the latter.

The invention will be better understood with the aid of the following description of a non-limiting method of implementation, with reference to the attached drawings in which:

FIG. 1 is a perspective view of a tibial plateau;

FIG. 2 is a side view of a crosspiece according to the invention;

FIG. 3 is a plan view of a crosspiece according to the invention.

The tibial plateau, indicated generally by (1), can either be of a monobloc synthetic material or be composed of a synthetic upper plate (2) and a metallic lower plate (3).

In the case of a synthetic monobloc plateau, a channel (4) receives a metal wire for the positioning of the plateau by radiography.

On its face bearing on the tibia, the plateau comprises dovetailed grooves (5) which form a grid pattern, at right angles or otherwise.

FIGS. 2 and 3 show an anchoring device 7 according to the present invention. In FIG. 2, the end of the anchoring device at the top of the Figure is the proximal end of the anchoring device, and the end of the device at the bottom of the Figure is the distal end, which is adapted to be inserted into a bone. At the proximal end of the anchoring device 7 is a stud 6 which is adapted to cooperate with one of the dovetailed grooves 5 in the tibial plateau 1. Extending from the stud 6 to the distal end of the anchoring device 7 is a central member 17. Extending radially from the central member 17 is a plurality of plane wings 8, 9, 10, 11. In the preferred embodiment shown, the four plane wings 8, 9, 10, 11 form a crosspiece.

FIG. 3 is a top view of the anchoring device of the present invention. To be noted is that the stud 6, while retaining a dovetailed profile so as to fit into one of the dovetailed grooves 5, is preferably elongated in one direction, as shown. This operates to prevent rotation of the anchoring device 7 relative to the tibial plateau 1 when the prosthesis is installed.

The wings 8, 9, 10, 11 preferably include a plurality of openings 12 therein, which permits the passage of regenerated bone when the anchoring device is installed.

This crosspiece is inserted with force into the cleaned and flattened upper face of the tibia which is to receive the tibial plateau.

In order to facilitate its insertion, the crosspiece may possess slightly bevelled edges (13), the lateral cants (14) narrowing towards the bottom. This insertion can also be facilitated by a central bore (15) extending through the stud 6 and central member 17.

This crosspiece can be made of any material, for example of titanium.

It is also conceivable, in an entirely exceptional manner, to use this crosspiece without fixation to the tibial plateau.

It has several advantages, such as:

anchoring and fixation of the tibial plateau by natural osseous locking;
stability of tibial plateau by osseous rehabilitation;
regeneration of the natural tibial plateau by osseous stress.

I claim:

1. An anchoring device for a knee prosthesis of the unicompartmental or bicompartmental type, the prosthesis including a tibial plateau having a tibial bearing face provided with anchoring grooves of a dovetailed profile forming a grid pattern, comprising an anchoring crosspiece having proximal and distal ends, the distal end of the crosspiece adapted to be inserted in a tibia, and the proximal end of the crosspiece including a stud adapted to fit in one of the grooves in the tibial bearing face, and a plurality of plane wings intersecting along an axis extending from the stud to the distal end.

2. An anchoring device according to claim 1, wherein the plane wings are provided with openings.

3. An anchoring device according to claim 1, wherein the plane wings of the crosssspiece have slightly bevelled edges nd lateral cants narrowing towards the distal end.

4. An anchoring device according to claim 1, including a cylindrical bore defined at the intersection of the plane wings.

5. An anchoring device according to claim 1, wherein the plane wings are arranged to be perpendicular to the tibial bearing face.

6. An anchoring device for a prosthesis to be installed in a bone, the anchoring device having a distal end adapted to be inserted into the bone and a proximal end, comprising:

a stud defined at the proximal end, the stud being shaped to engage the prosthesis;
a central member extending from the stud to the distal end; and
a plurality of plane wings extending from the central member such that the central member forms a planar intersection of the plane wings, the plane wings being adapted to engage the interior structure of the bone.

7. An anchoring device according to claim 6, wherein four plane wings are arranged in a cross.

8. An anchoring device according to claim 6, further including a plurality of openings defined in at least one of the plane wings.

9. An anchoring device according to claim 6, further including a bore extending through the stud and the central member.

10. An anchoring device according to claim 6, wherein at least one of the plane wings includes at least one bevelled edge.

11. An anchoring device according to claim 6, wherein the plane wings are narrower toward the distal end than toward the proximal end.

12. An anchoring device according to claim 6, wherein the stud is shaped to be complementary to a dovetailed groove.

13. An anchoring device according to claim 12, wherein the stud is elongated in a direction perpendicular to the central member.

14. A prosthesis adapted to be installed in a bone, comprising:
   a plateau member, adapted to be disposed generally on a surface of the bone and having a bearing surface for contact with the bone, the bearing surface having defined therein at least one groove having a dovetailed profile; and
   an anchoring device, having a distal end adapted to be inserted into the bone and a proximal end, including:
   (a) a stud defined at the proximal end, the stud being shaped to be complementary to at least one groove in the bearing surface of the plateau member,
   (b) a central member, extending from the stud toward the distal end, and
   (c) a plurality of plane wings extending from the central member such that the central member forms a planar intersection of the wings, the plane wings being adapted to engage the structure of the bone.

15. A prosthesis according to claim 14, wherein the plane wings are disposed perpendicular to the bearing surface.

16. A prosthesis according to claim 14, further including a plurality of openings defined in at least one of the plane wings.

17. A prosthesis according to claim 14, further including a bore extending through the stud and the central member of the anchoring device.

18. A prosthesis according to claim 14, wherein the plane wings of the anchoring device include at least one bevelled edge.

19. A prosthesis according to claim 14, wherein the plane wings of the anchoring device are narrower at the distal end than toward the proximal end.

20. A prosthesis according to claim 14, wherein the stud of the anchoring device is elongated in a direction perpendicular to the central member.

* * * * *